US008553217B2

(12) United States Patent
Chuang et al.

(10) Patent No.: US 8,553,217 B2
(45) Date of Patent: Oct. 8, 2013

(54) EUV HIGH THROUGHPUT INSPECTION SYSTEM FOR DEFECT DETECTION ON PATTERNED EUV MASKS, MASK BLANKS, AND WAFERS

(75) Inventors: Yung-Ho Chuang, Cupertino, CA (US); Richard W. Solarz, Danville, CA (US); David R. Shafer, Fairfield, CT (US); Bin-Ming Benjamin Tsai, Saratoga, CA (US); David L. Brown, Sunnyvale, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 250 days.

(21) Appl. No.: 12/812,950

(22) PCT Filed: Jun. 18, 2010

(86) PCT No.: PCT/US2010/039150
§ 371 (c)(1),
(2), (4) Date: Jul. 14, 2010

(87) PCT Pub. No.: WO2010/148293
PCT Pub. Date: Dec. 23, 2010

(65) Prior Publication Data
US 2011/0116077 A1    May 19, 2011

Related U.S. Application Data

(60) Provisional application No. 61/218,900, filed on Jun. 19, 2009.

(51) Int. Cl.
*G01N 21/00* (2006.01)
(52) U.S. Cl.
USPC ..................................... 356/237.5

(58) Field of Classification Search
USPC ..................................... 356/237.5
See application file for complete search history.

(56) References Cited

U.S. PATENT DOCUMENTS 4,173,399 A * 11/1979 Yevick ........................ 353/78
5,071,240 A   12/1991 Ichihara et al.
(Continued)

FOREIGN PATENT DOCUMENTS

DE    10220815 A1    11/2003
DE    10345783 A1    4/2005
(Continued)

OTHER PUBLICATIONS

International Search Report for PCT/EP2010/004519 dated Sep. 20, 2010.

(Continued)

*Primary Examiner* — Tu Nguyen
(74) *Attorney, Agent, or Firm* — Bever, Hoffman & Harms, LLP; Jeanette S. Harms

(57) ABSTRACT

Inspection of EUV patterned masks, blank masks, and patterned wafers generated by EUV patterned masks requires high magnification and a large field of view at the image plane. An EUV inspection system can include a light source directed to an inspected surface, a detector for detecting light deflected from the inspected surface, and an optic configuration for directing the light from the inspected surface to the detector. In particular, the detector can include a plurality of sensor modules. Additionally, the optic configuration can include a plurality of mirrors that provide magnification of at least 100× within an optical path less than 5 meters long. In one embodiment, the optical path is approximately 2-3 meters long.

56 Claims, 19 Drawing Sheets

(56) References Cited

U.S. PATENT DOCUMENTS

| | | | |
|---|---|---|---|
| 5,113,284 A * | 5/1992 | Stuhlinger | 359/419 |
| 5,291,340 A | 3/1994 | Kashima | |
| 6,002,740 A | 12/1999 | Cerrina et al. | |
| 6,238,830 B1 | 5/2001 | Rangarajan et al. | |
| 6,555,828 B1 | 4/2003 | Bokor et al. | |
| 6,583,068 B2 | 6/2003 | Yan et al. | |
| 6,603,543 B1 | 8/2003 | La Fontaine | |
| 6,894,834 B2 | 5/2005 | Mann et al. | |
| 6,954,266 B2 | 10/2005 | Tomie | |
| 6,963,395 B2 | 11/2005 | Goldberg | |
| 7,005,649 B1 | 2/2006 | Tezuka et al. | |
| 7,179,568 B2 | 2/2007 | Cerrina et al. | |
| 7,220,969 B2 | 5/2007 | Tezuka et al. | |
| 7,268,945 B2 | 9/2007 | Yun et al. | |
| 7,623,620 B2 | 11/2009 | Mann et al. | |
| 7,649,625 B2 | 1/2010 | Takada | |
| 2002/0018289 A1 * | 2/2002 | Nanba et al. | 359/365 |
| 2003/0007255 A1 * | 1/2003 | Akiyama et al. | 359/676 |
| 2003/0043370 A1 | 3/2003 | Goldberg | |
| 2003/0067598 A1 | 4/2003 | Tomie | |
| 2004/0165165 A1 | 8/2004 | Yun et al. | |
| 2005/0008944 A1 | 1/2005 | Cerrina et al. | |
| 2005/0201514 A1 | 9/2005 | Mann et al. | |
| 2006/0054836 A1 | 3/2006 | Tezuka et al. | |
| 2006/0072806 A1 | 4/2006 | Lin | |
| 2006/0138338 A1 | 6/2006 | Tezuka et al. | |
| 2007/0064997 A1 | 3/2007 | Itoh | |
| 2008/0078941 A1 | 4/2008 | Goodwin | |
| 2008/0119060 A1 | 5/2008 | Goodwin | |
| 2008/0266654 A1 | 10/2008 | Banine et al. | |
| 2009/0046280 A1 | 2/2009 | Tsutsui et al. | |
| 2009/0091723 A1 * | 4/2009 | Sasaki | 355/53 |
| 2009/0168152 A1 | 7/2009 | Gelernt et al. | |
| 2012/0140454 A1 | 6/2012 | Mann | |

FOREIGN PATENT DOCUMENTS

| | | |
|---|---|---|
| DE | 102006059436 A1 | 6/2008 |
| JP | 2006-080437 A | 3/2006 |
| JP | 2007-058130 A | 3/2007 |
| JP | 2009-092407 A | 4/2009 |
| WO | WO2005/096060 A1 | 10/2005 |
| WO | WO2006/069725 A1 | 7/2006 |

OTHER PUBLICATIONS

Gross, H., Handbook of Optical Systems, vol. 1, Wiley-VCH-Verlag, Weinheim, 2005, p. 514, formula 11-37.

* cited by examiner

110

| SRF | Radius | Thickness | Aperture Radius | Glass |
|---|---|---|---|---|
| OBJ | --- | 15.000008 V | 8.000000 | AIR |
| 1 | -70.000000 V | 66.837552 V | 11.872985 S | AIR |
| 2 | -87.371080 V | -66.837552 P | 29.130367 S | REFLECT |
| 3 | -78.008569 V | 156.490199 V | 10.298685 S | REFLECT |
| 4 | -216.000000 V | 93.418488 V | 54.827199 S | AIR |
| 5 | -190.035692 V | -93.418448 P | 88.642837 S | REFLECT |
| 6 | -281.681911 V | 96.656458 V | 40.000000 | REFLECT |
| AST | --- | 2.5000e+03 V | 8.618656 AS | AIR |
| IMS | --- | --- | 796.231914 S | --- |

FIG. 1B

| SRF | AS0 | AS1 | AS2 | AS3 | AS4 | AS5 |
|---|---|---|---|---|---|---|
| 2 | --- | --- | -1.6062e-08 | -2.6641e-12 | -4.5275e-16 | 4.1829e-21 |
| 3 | --- | --- | -1.7409e-06 | -7.3382e-10 | -8.2941e-13 | 1.3239e-16 |
| 5 | --- | --- | 3.3498e-09 | 1.8651e-13 | 8.6775e-19 | 3.2194e-22 |
| 6 | --- | --- | 1.0429e-07 | -6.9310e-12 | --- | --- |

| SRF | Radius | Thickness | Aperture Radius | Glass |
|---|---|---|---|---|
| OBJ | --- | 14.99980 | 8.000000 | AIR |
| 1 | -70.000000 V | 67.339667 | 11.872955 S | AIR |
| AST | -86.985414 | -67.339667 P | 29.259982 AS | REFLECT |
| 3 | -81.65574 | 159.744887 | 10.116607 S | REFLECT |
| 4 | -216.000000 V | 94.925563 | 59.621505 S | AIR |
| 5 | -190.900162 | -94.925563 P | 95.849079 S | REFLECT |
| 6 | -236.640793 | 100.399521 | 40.000000 | REFLECT |
| 7 | --- | 395.458806 V | 8.409850 S | AIR |
| 8 | --- | --- | 8.000000 | AIR |
| 9 | 42.570333 V | -45.191940 V | 3.000000 | REFLECT |
| 10 | --- | --- | 8.000000 | AIR |
| 11 | 77.534980 V | 1.8977e+03 V | 3.000000 | REFLECT |
| 12 | --- | --- | 3.000000 | AIR |
| IMS | --- | --- | 50.000000 | --- |

FIG. 2B

| SRF | AS0 | AS1 | AS2 | AS3 | AS4 | AS5 |
|---|---|---|---|---|---|---|
| 2 | --- | --- | -1.3237e-08 | -2.3364e-12 | -3.5229e-16 | -4.8609e-20 |
| 3 | --- | --- | -1.8165e-06 | -7.0065e-10 | -1.0063e-12 | 7.7517e-16 |
| 5 | --- | --- | 2.8236e-09 | 1.2428e-13 | 1.7187e-18 | 1.6513e-22 |
| 6 | --- | --- | 1.2594e-07 | -8.9335e-12 | 5.9190e-16 | -1.8837e-20 |

| SRF | DT | DCX | DCY | DCZ | TLA | TLB | TLC |
|---|---|---|---|---|---|---|---|
| 8 | 1 | --- | 118.388718 | --- | --- | --- | --- |
| 9 | 1 | --- | --- | --- | -1.286052 | --- | --- |
| 10 | 1 | --- | 13.529076 | --- | --- | --- | --- |
| 11 | 1 | --- | --- | --- | -11.957296 | --- | --- |
| 13 | 1 | --- | 568.110319 | --- | 15.355394 | --- | --- |

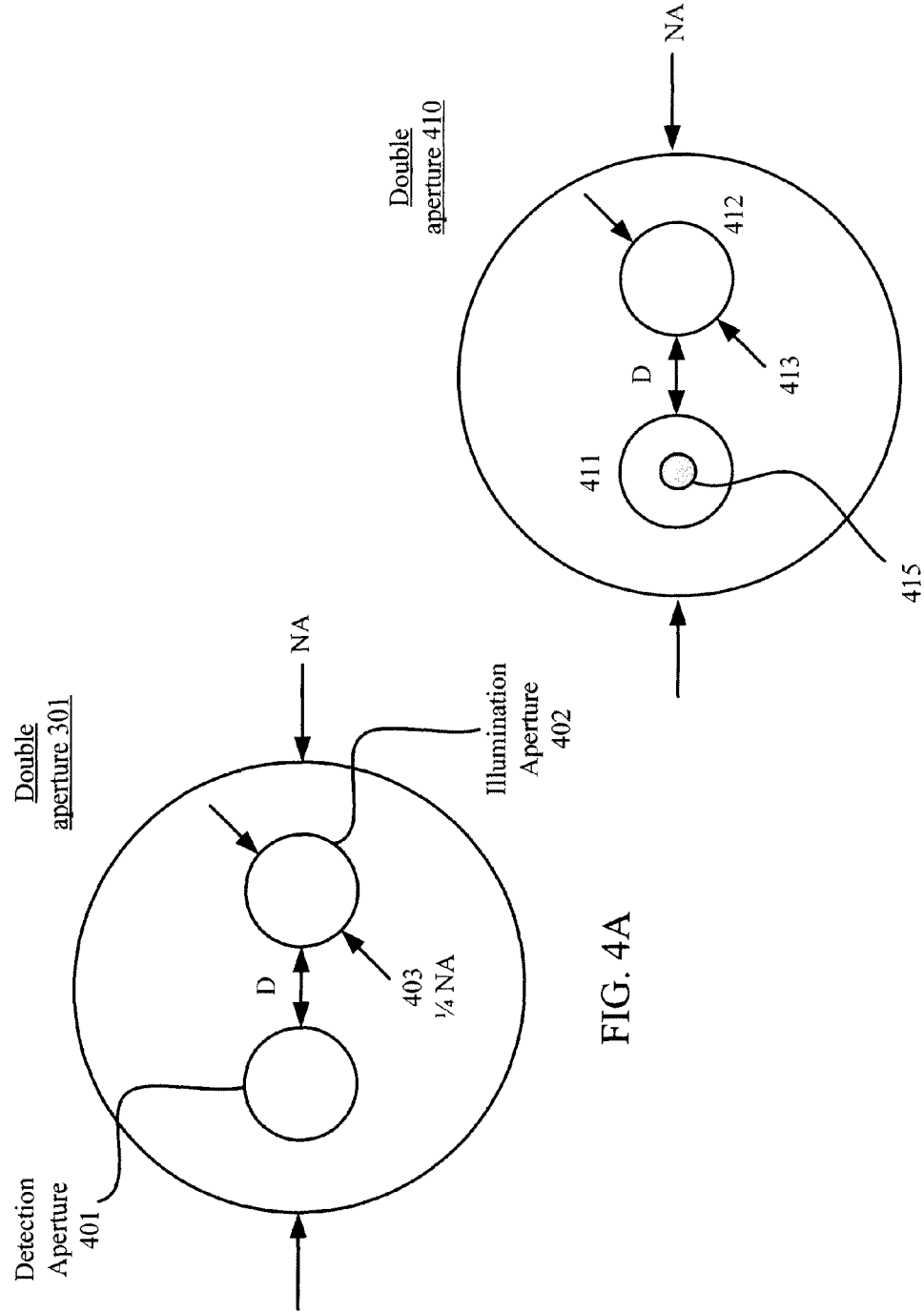

510

| SRF | Radius | Thickness | Aperture Radius | Glass |
|---|---|---|---|---|
| OBJ | --- | 2.8430e+03 | 41.256336 | AIR |
| 1 | --- | 150.000000 | 3.178107 S | AIR |
| 2 | 22.000000 | -112.048308 V | 1.169055 S | REFLECT |
| 3 | 152.708240 V | 112.048308 P | 11.576555 S | REFLECT |
| 4 | 22.000000 P | -112.048308 P | 4.995667 S | REFLECT |
| AST | 152.708240 P | 112.048308 P | 49.301693 AS | REFLECT |
| 6 | 22.000000 | 85.158579 V | 21.320864 S | AIR |
| IMS | --- | --- | 0.55031 S | --- |

| SRF | CC | AD | AE | AF | AG |
|---|---|---|---|---|---|
| 3 | -3.1444e-02 | --- | --- | --- | --- |
| 5 | -3.1444e-02 | --- | --- | --- | --- |

| SRF | Radius | Thickness | Aperture Radius | Glass |
|---|---|---|---|---|
| OBJ | --- | 2.2000e +20 | 3.0720e+18 | AIR |
| 3 | 22.000000 | -112.148740 V | 1.174599 S | REFLECT |
| 4 | 152.705863 V | 112.148740 P | 11.584046 S | REFLECT |
| 5 | 22.000000 | -112.148740 P | 4.978610 S | REFLECT |
| AST | 152.705863 P | 112.148740 P | 49.131796 AS | REFLECT |
| 7 | 22.000000 | 84.775153 V | 21.182947 S | AIR |
| 8 | --- | --- | 0.056001 S | AIR |

| SRF | CC | AD | AE | AF | AG |
|---|---|---|---|---|---|
| 4 | -3.1025e-02 | --- | --- | --- | --- |
| 6 | -3.1025e-02 | --- | --- | --- | --- |

| SRF | Radius | Thickness | Aperture Radius | Glass |
|---|---|---|---|---|
| OBJ | --- | 388.000000 | 5.49619 | AIR |
| 1 | 22.000000 | -112.051477 V | 5.000000 | REFLECT |
| 2 | 152.704897 | 112.051477 V | 50.000000 X | REFLECT |
| 3 | 22.000000 | -112.051477 V | 5.000000 | REFLECT |
| AST | 152.705863 P | 112.051477 V | 50.000000 X | REFLECT |
| 5 | 22.000000 | 85.169910 | 21.323764 S | AIR |
| IMS | --- | --- | 0.055029 S | --- |

| SRF | CC | AD | AE | AF | AG |
|---|---|---|---|---|---|
| 2 | -3.1462e-02 | --- | --- | --- | --- |
| 4 | -3.1462e-02 | --- | --- | --- | --- |

FIG. 7B

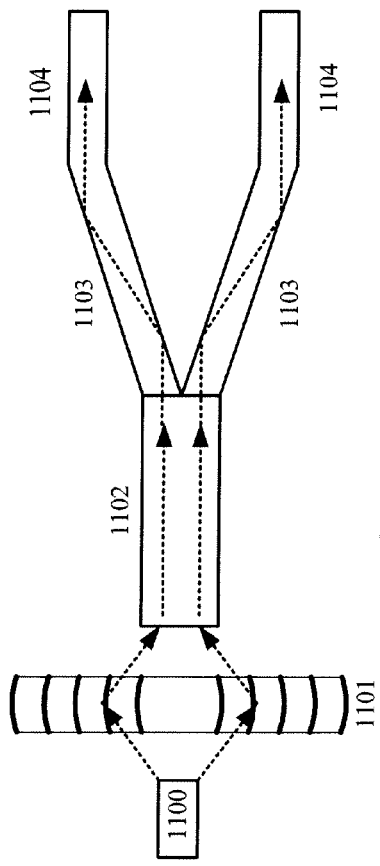
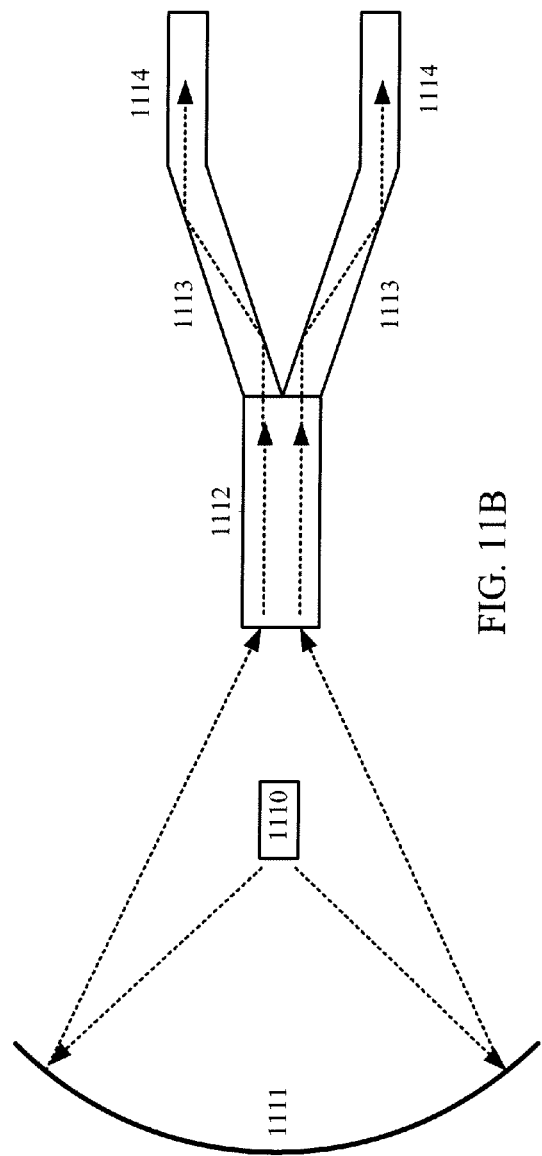
FIG. 11A
FIG. 11B

EUV HIGH THROUGHPUT INSPECTION SYSTEM FOR DEFECT DETECTION ON PATTERNED EUV MASKS, MASK BLANKS, AND WAFERS

RELATED APPLICATIONS

This application claims priority of U.S. Provisional Patent Application Ser. No. 61/218,900 entitled "Inspection System For Defect Detection On Patterned EUV Masks, Mask Blanks, And Wafers" filed Jun. 19, 2009 and PCT Application serial no. PCT/US10/39150 entitled "EUV High Throughput Inspection System For Defect Detection On Patterned EUV Masks, Mask Blanks, And Wafers" filed Jun. 18, 2010.

BACKGROUND OF THE INVENTION

1. Field of the Invention

The present invention relates to an inspection system, and in particular to an extreme ultraviolet (EUV) high throughput inspection system.

2. Related Art

Current patterned mask inspection is typically accomplished using transmissive optics and coherent sources. Specifically, the large magnifications provided by transmissive microscopes of moderate NA (numerical aperture) systems coupled to deep UV (ultraviolet radiation, e.g. 257 nm, 193 nm, etc.) coherent illumination sources has been sufficient to provide the sensitivity required for mask defect detection for microelectronics fabricated using excimer laser-based steppers. Moreover, the combined high magnification of the transmissive microscopes and the high brightness of the illumination sources have provided sufficient image throughput to ensure cost effective mask inspection systems for deep UV mask inspection.

Extreme ultraviolet (EUV) mask inspection systems are known. Unfortunately, the optics of these systems are relatively low resolution and have an inadequate field of view at the image plane for the cost-effective inspection of EUV patterned masks. Therefore, a need arises for an inspection system with a field of view at the image plane consistent with high resolution and cost-effective EUV patterned mask, mask blank, and wafer inspection.

EUV sources of high average power have been previously described in lithography applications with etendue (i.e. light spread as defined by area and angle) requirements of 1-3.3 $mm^2$-sr and average power of 210 W at 13.4 mm at the intermediate focus. These EUV sources have typically included discharge-driven or laser-driven plasmas. Unfortunately, none of these EUV sources can efficiently generate radiation within the etendue required for EUV mask inspection applications because the conversion efficiency of lasers or discharges to EUV photons is highly inefficient, e.g. in the range of only 1-3% conversion. Therefore, a further need arises for an EUV source that can minimize power consumption. In particular, a need arises for a laser driver of average power and repetition rate that also minimizes debris effects on the collector optics.

As noted above, conventional inspection systems use coherent sources of wavelengths, e.g. ≥193 nm. However, state of the art masks are being produced using EUV radiation at ≤13 nm. With two such disparate wavelengths, the inspection of masks with conventional inspection systems can be problematic, particularly with regard to the interpretation and rendering of optical proximity effects. In other words, the sensitivity of the 193 nm based mask inspection systems can be inadequate for EUV masks with features on the order of 13 nm. Therefore, a further need arises for an illumination source that can provide adequate sensitivity for the inspection of EUV masks.

SUMMARY OF THE INVENTION

Inspection of EUV patterned masks, blank masks, and patterned wafers generated by EUV patterned masks requires high magnification and a large field of view at the image plane. The inspection systems described herein can include a light source directed to an inspected surface, a detector for detecting light deflected from the inspected surface, and an optic configuration for directing the light from the inspected surface to the detector. In particular, the detector can include a plurality of sensor modules. Additionally, the optic configuration can include a plurality of mirrors that provide magnification of at least 100× within an optical path less than 5 meters long. In one embodiment, the optical path is approximately 2-3 meters long.

In one embodiment, an EUV inspection system can include a four mirror, four bounce, unobscured optic configuration. In another embodiment, an EUV inspection system can include a four mirror, four bounce, unobscured optic configuration as well as a scintillator (or photocathode) and a magnifying system. In another embodiment, an EUV inspection system can include a six mirror, six bounce, unobscured optic configuration. In yet another embodiment, an EUV inspection system can include a two mirror, four bounce, obscured optic configuration.

In one embodiment, which can be used for both unobscured and obscured optic configurations, a double aperture component can be included in the beam path for pupil shaping, thereby facilitating aerial imaging while correcting for the keystone distortion resulting from imaging at an angle.

The double aperture component includes an illumination aperture and a detection aperture. For obscured lithographic configurations, an obscuration in the detection aperture is provided. Notably, different sizes of the aperture openings and the distance between these apertures can advantageously match conditions associated with different steppers/scanners.

A high brightness laser-pumped EUV plasma can provide the EUV inspection illumination (i.e. the light source) at the required etendue for EUV mask/wafer inspection. This radiation can be generated using a cost-effective laser driver. For example, the laser can be ytterbium (Yb)-based or neodymium (Nd)-based. The laser can be operated at repetition rates in excess of 5 kHz while still using a minimal, average power between 1-4 kilowatts. In one embodiment, the laser can use pulses less than 4 nsec with the EUV emitter to generate the plasma. The EUV emitter can be tin (Sn), xenon (Xe), or lithium (Li), or a target doped with Sn, Xe, and/or Li. Droplet sizes between 35-50 microns can be used. The illumination of the EUV emitter has a spot size on the target between 30-50 microns. In other embodiments, the light source can include one of a laser-produced plasma (LPP) source, a discharge produced plasma (DPP) light source, and a plasma lens light source.

Notably, the light source can be configured to distribute light on the inspected surface to facilitate heat dissipation on the inspected surface. In one embodiment, the light source can include a plurality of light tubes. In another embodiment, the light source can include an aperture set, wherein each aperture (with a predetermined magnification) substantially matches a sensor shape.

The detector subsystem can include a modular array of sensors. In one embodiment, the modular array can include plurality of sensor modules in a single row (interleaved configuration). In another embodiment, the modular array can include the plurality of sensor modules positioned in at least two rows, wherein the sensor modules of one row are offset vertically with respect to the sensor modules of any adjacent row(s) and the sensor modules of every other row are aligned vertically (high speed configuration). In yet another embodiment, the modular array including the plurality of sensor modules positioned in at least two rows, wherein the sensor modules of one row are vertically aligned with respect to the sensor modules of any adjacent row(s) (high integration configuration).

BRIEF DESCRIPTION OF THE FIGURES

FIG. 1B shows a prescription for the optic configuration of FIG. 1A.

FIG. 1C shows the aspheric surface data for certain surfaces of FIG. 1B.

FIG. 2B shows a prescription for the optic configuration of FIG. 2A.

FIG. 2C shows the aspheric surface data for certain surfaces of FIG. 2B.

FIG. 2D shows the decenter data and the tilt data for certain surfaces of FIG. 2B.

FIGS. 4A and 4B illustrate exemplary double aperture components usable in imaging systems.

FIG. 5B shows a prescription for the optic configuration of FIG. 5A.

FIG. 5C shows the conic and polynomial aspheric data for certain surfaces of FIG. 5B.

FIG. 6A shows another prescription for the optic configuration of FIG. 5A.

FIG. 6B shows the conic and polynomial aspheric data for certain surfaces of FIG. 6A.

FIG. 7A shows yet another prescription for the optic configuration of FIG. 5A.

FIG. 7B shows the conic and polynomial aspheric data for certain surfaces of FIG. 7A.

FIGS. 11A and 11B illustrate exemplary hollow light pipe configurations.

DETAILED DESCRIPTION OF THE FIGURES

Figure 1A:
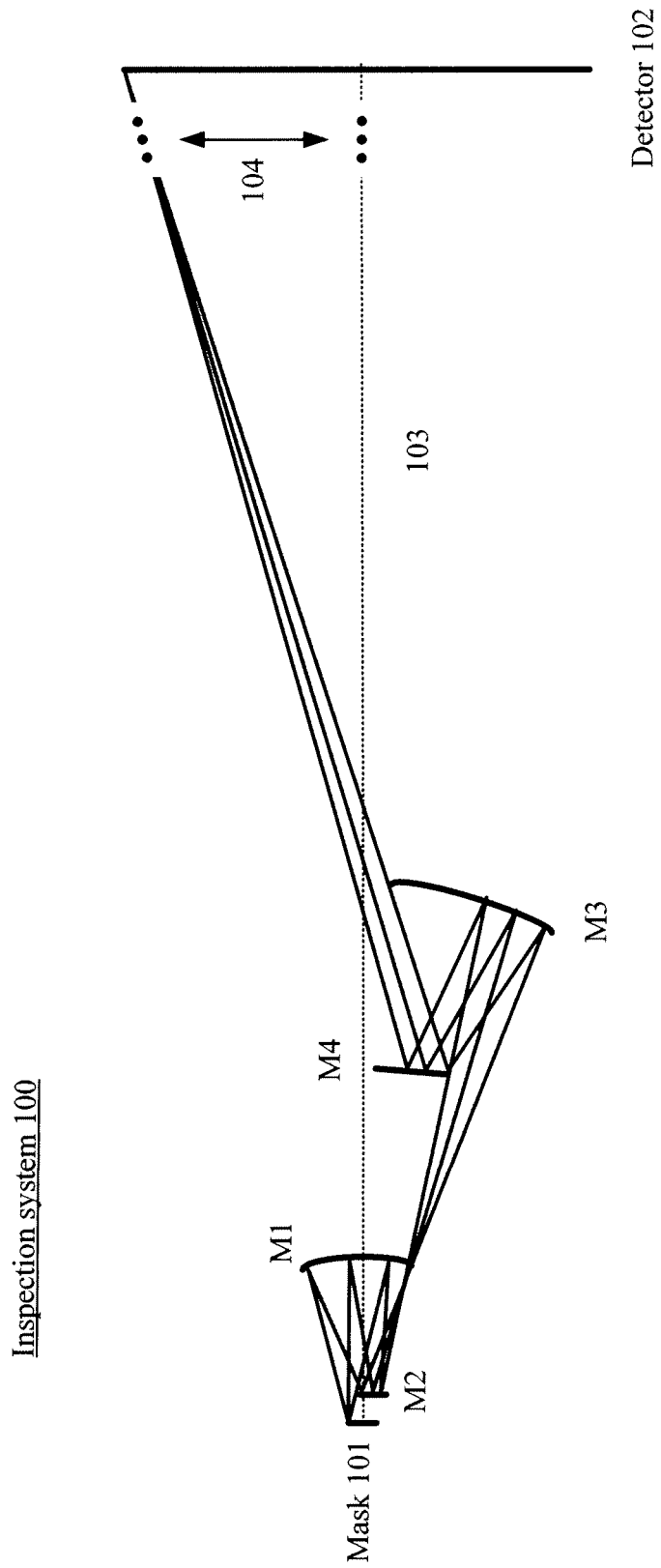
FIG. 1A illustrates an exemplary inspection system including an unobscured optic configuration having four mirrors.

The inspection of EUV masks using actinic radiation (13 nm) poses a number of challenges and departures from mask inspection technology for earlier inspected nodes. Exemplary optic designs and characteristics for an inspection system are described herein. These optic designs and characteristics can be used to perform photomask blank inspection, patterned photomask inspection, aerial imaging of photomasks, and general wafer inspection FIG. 1A illustrates an exemplary inspection system 100 including a unobscured optic configuration. In this embodiment, inspection system 100 includes four mirrors M1, M2, M3, M4, which reflect light beams from a mask 101 to substantially a point on a detector 102. Note that standard nomenclature regarding mirrors is used herein, i.e. the mirror receiving and reflecting the light from the inspected surface is designated M1, the mirror receiving and reflecting the light from mirror M1 is designated M2, and so forth. Note that in this optic configuration, an illumination source generates light 103, which may pass through holes of one or more of mirrors M1, M2, M3, and M4 (M3 and M4 shown in this exemplary configuration). This illumination source can be substantially in the same position as detector 102 and therefore is not shown for simplicity. Notably, the detected light is not obscured by the optical system and thus the optic configuration can be characterized as being unobscured.

Note that the distance from mask 101 to detector 102 is actually much longer, as indicated by areas 104, if shown to scale relative to mirrors M1-M4. In other words, FIG. 1A is provided to demonstrate the relative placement of mask 101 and mirrors M1-M4 rather than the distance from mask 101 to detector 102. For example, in this embodiment, the distance from mask 101 (OBJ) to detector 102 is 2500 mm.

The prescription for the optic configuration shown in FIG. 1A is shown in a table 110 of FIG. 1B. The optic configurations described herein are described using OSLO (Optics Software for Layout and Optimization) files, which are well known to those skilled in the art of optic design. Thus, SRF designates each surface in the optic configuration. Note that optical elements other than mirrors are described in table 110, but are not shown in FIG. 1A for simplicity.

In table 110, the Glass designation refers to a reflective surface REFLECT (for mirrors) or a bending surface AIR (which mathematically is also characterized as a surface). Radius refers to the radius of curvature of the surface, Thickness refers to the distance (in mm) to the next surface, Aperture Radius is the radius of the aperture of that surface. OBJ refers to the object (surface zero) (e.g. the mask or wafer), AS and AST refers to an aperture stop, IMS refers to detector 102 (i.e. the image sensor), V refers to a design variable (which is optimized to produce the best optical system performance), P refers to "pick-up" variable (which is the same value of the previous surface), and S refers to a mathematically solved ray bundle size for the aperture. The "- - -" indicates that a specific surface does not have a corresponding parameter (e.g. OBJ does not have a radius of curvature). The aspheric surface data of specific surfaces, i.e. 2, 3, 5, and 6 is shown in a table 120 of FIG. 1C. Note that AS0, AS1, AS2, AS3, AS4, and AS5 refer to asphere parameters, which are known to those skilled in the art of optics.

Figure 1D:
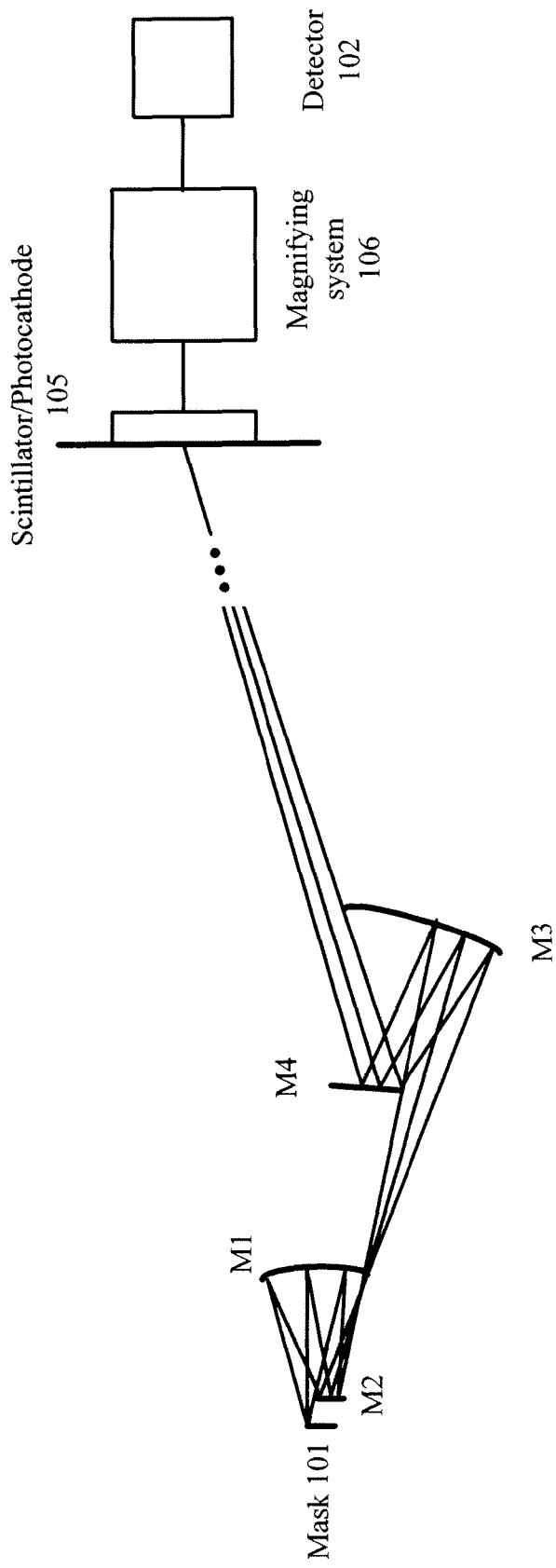
FIG. 1D illustrates an exemplary inspection including an unobscured optic configuration having four mirrors, a scintillator (or photocathode), and a magnifying system.

In this configuration, inspection system 100 can provide a 100× magnification and has a 0.25 NA. Inspection system 100 can provide a wavefront correction of better than 0.03 waves rms (at 13 nm) over a 74 mm×18.5 mm detector plane. In this embodiment, the distance from mask 101 (OBJ) to detector 102 is approximately 2-3 m. In one embodiment shown in FIG. 1D, magnification can be further increased by including a scintillator 105 (to convert EUV radiation into visible light) and at least one magnifying system 106 (e.g. a visible microscope), both of which are positioned before detector 102. In another embodiment, the magnification can also be increased by including a micro-channel plate (photocathode array that converts the detected light into electrons) with electromagnetic zooms (x-ray zoom tube) to implement magnifying system 106. In one embodiment, the addition of scintillator/photocathode 105 and magnifying system 106 can increase the magnification to between 500×-10000×.

Figure 2A:
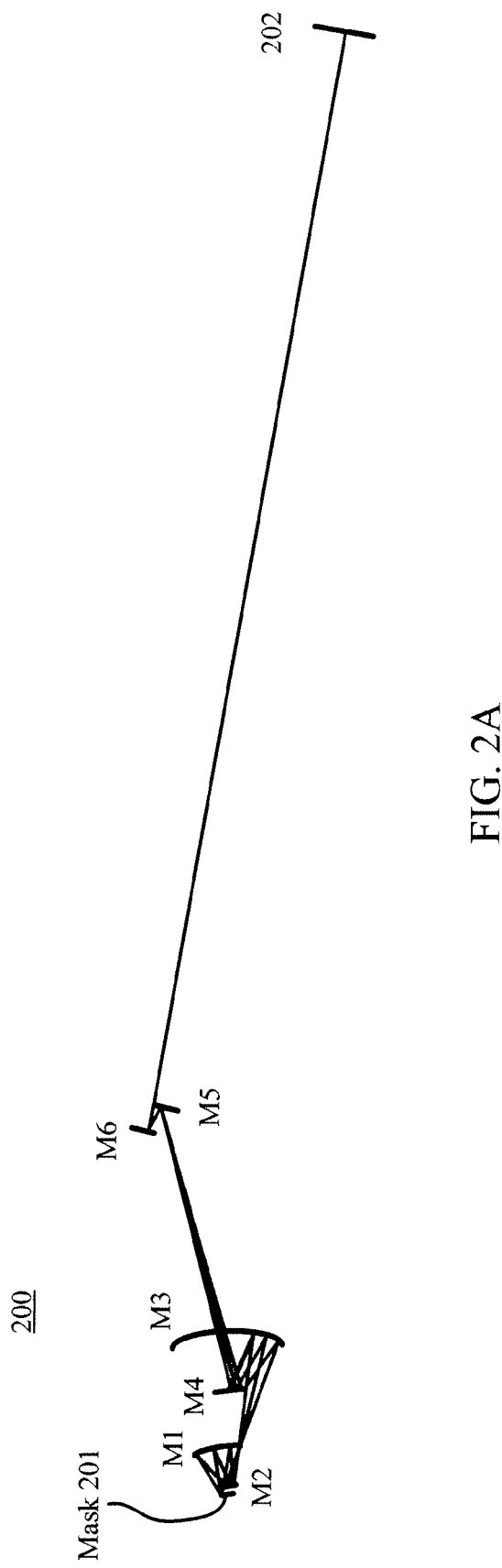
FIG. 2A illustrates an exemplary inspection system including an unobscured optic configuration having six mirrors.

FIG. 2A illustrates an exemplary inspection system 200 including a unobscured optic configuration. In this embodiment, inspection system 200 includes six mirrors M1, M2, M3, M4, M5, and M6 which reflect light beams from a mask 201 to a detector 202 using six bounces. Note that mirrors M1, M2, M3, and M4 are positioned to facilitate the bouncing in a similar manner to that shown for inspection system 100 (FIG. 1A) and therefore this area of the optic configuration effectively shown in greater detail in FIG. 1A. The prescription for the optic configuration shown in FIG. 2A is shown in a table 210 of FIG. 2B. The aspheric surface data of specific surfaces, i.e. 2, 3, 5, and 6 are shown in a table 220 of FIG. 2C. The decenter data (DCX, DCY, DCZ) and the tilt data (TLA, TLB, TLC) of specific surfaces, i.e. 8, 9, 10, 11, and 13, are shown in a table 230 of FIG. 2D. DT in table 220 indicates a decenter/tilt order, e.g. because DT=1, the decenter should be performed before the tilt.

In this configuration, inspection system 200 can provide a 1000× magnification and has a 0.25 NA. Inspection system 200 can provide a wavefront correction of better than 0.03 waves rms (at 13 nm) over a 74 mm×18.5 mm detector plane. In this embodiment, the distance from mask 201 (OBJ) to detector 202 is approximately 2-3 m. Note that the mirrors M5 and M6, which are spherical mirrors, can act as retro-telephoto optics to reduce the total distance from mask 201 to detector 202.

Figure 3:
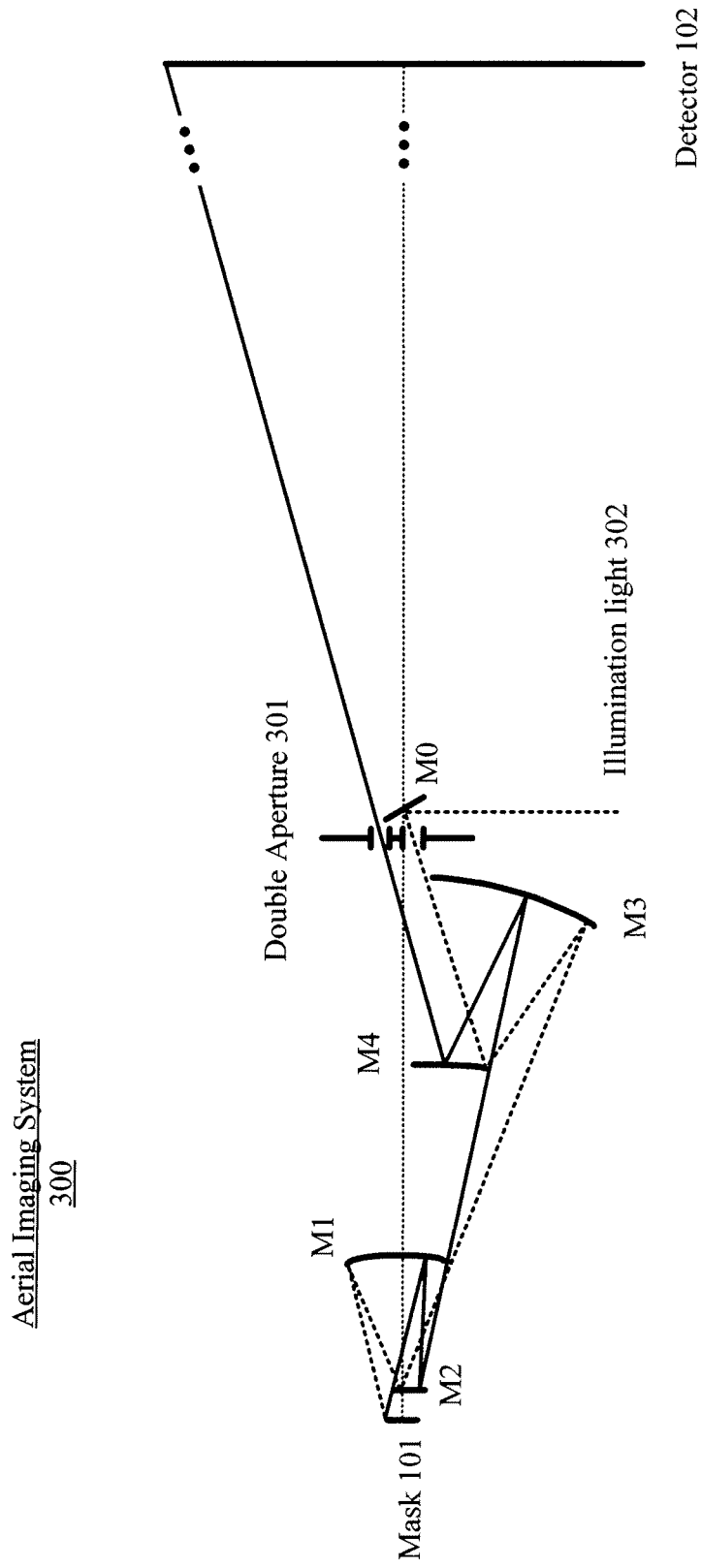
FIG. 3 illustrates the four mirror optic configuration of FIG. 1 including a double aperture component, thereby forming an imaging system.

FIG. 3 illustrates an exemplary aerial imaging system 300 including the optics described for inspection system 100 (e.g. mirrors M1, M2, M3, and M4 of FIG. 1A) and a double aperture component 301. FIG. 4A illustrates an exemplary double aperture component 301. In this embodiment, double aperture component 301 includes a detection aperture 401 and an illumination aperture 402. Referring back to FIG. 3, illumination aperture 402 receives an illumination light 302, which has been reflected by a mirror M0. Mirrors M4, M3, M2, and M1 (in that order) direct the light back to mask 101 (dotted line). The reflected light from mask 101 is then redirected back to detector 102 via mirrors M1, M2, M3, and M4 (in that order) (solid line). Notably, after being reflected by mirror M4, the reflected light passes through detection aperture 401 (see FIG. 4A) before impinging on detector 102.

In one embodiment, both detection aperture 401 and illumination aperture 402 have a diameter that is the same as the EUV lithography imaging NA at mask 101. In other words, the diameters of apertures 401 and 402 can be chosen to match the NA used for mask illumination in the actual stepper or scanner. For example, for a 0.25 NA lithographic system with demagnification factor 4×, the illumination opening can be 0.0625 NA. (Noting that the current example corresponds to 0.25 NA (Full), then the NA (Aperture)=0.25/4=0.0625 and illumination is at 6° angle. The angle can be changed by varying the distance between apertures.)

Notably, the use of this double aperture component and the distance D separating detection aperture 401 and illumination aperture 402 can advantageously correct for the keystone distortion resulting from imaging at an angle on mask 101. As a further advantage, both detection aperture 401 and illumination aperture 402 can shape the illumination beams, thereby facilitating accurate aerial imaging. Note that different size aperture openings and different distances D can compensate for conditions associated with different types of steppers/scanners.

In one embodiment where the EUV lithographic optics making the mask uses a central obscuration, a double aperture component with its own center obscuration can be used. FIG. 4B illustrates an exemplary double aperture component 410 that includes a detection aperture 411 and an illumination aperture 412. Note that detection aperture 411 and an illumination aperture 412 function similarly to detection aperture 401 and an illumination aperture 402 (FIG. 4A) and provide similar advantages.

Note that although double aperture 301 is described in reference to the optic configuration described for inspection system 100 (FIG. 1A), the use of a double aperture is applicable to all optic configurations described herein (e.g. FIGS. 1A, 1D, 2A, and 5A). When aperture 301 is included, the prescription for the optic configuration remains the same.

In one embodiment, both detection aperture 411 and illumination aperture 412 have a diameter that is the same as the EUV lithography imaging NA at the mask. The distance D separating detection aperture 411 and illumination aperture 412 can be determined by the EUV lithography illumination angle on the mask. Notably, both detection aperture 411 and illumination aperture 412 can shape the illumination beams, thereby providing accurate aerial imaging. For aerial imaging, the central obscuration ratio for detection aperture 411 and obscuration 415 is the same (i.e. size, position, etc) used for EUV lithography. In this manner, obscuration 415 can reproduce the conditions at EUV lithography systems using apertured illumination.

Figure 5A:
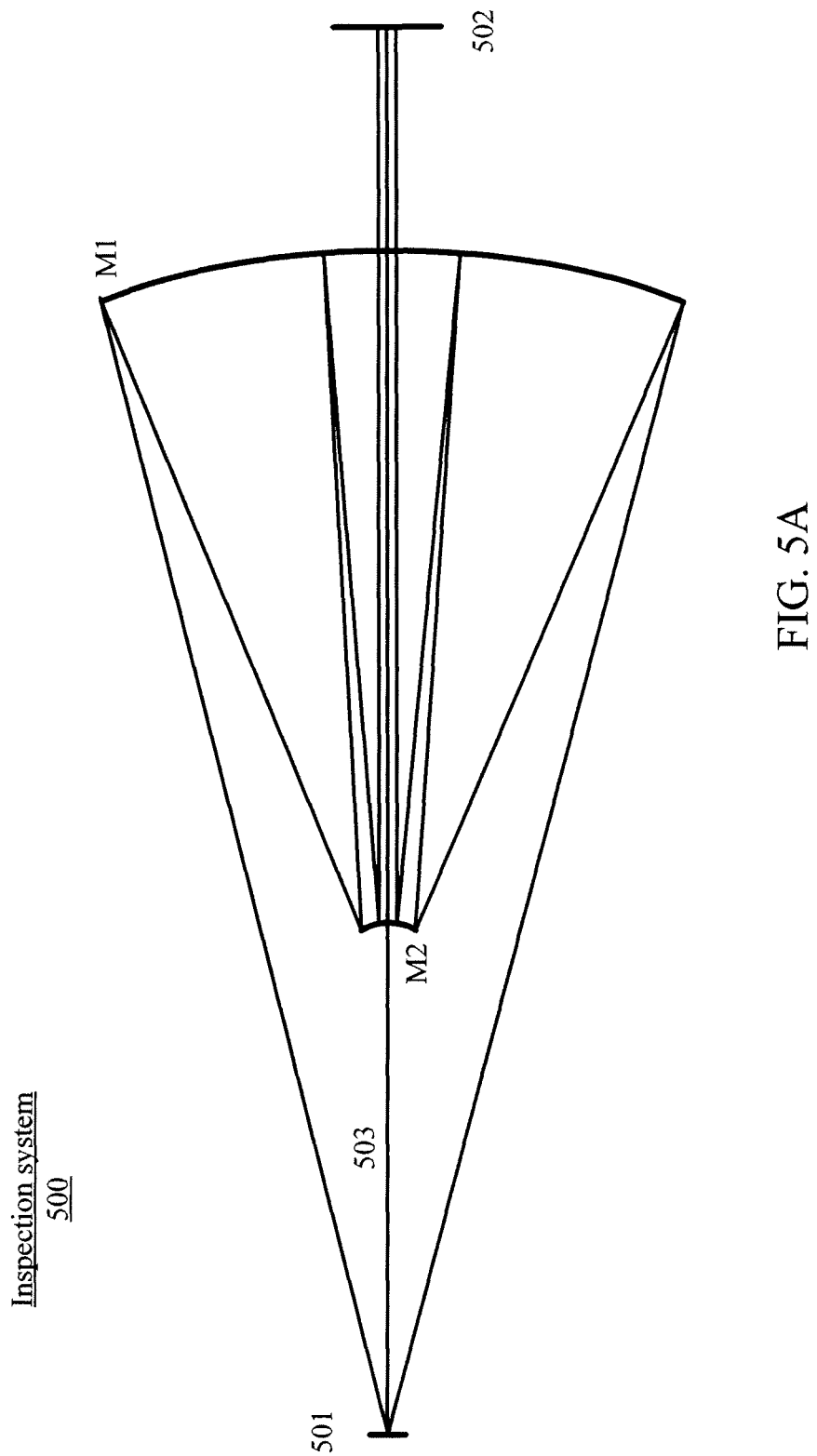
FIG. 5A illustrates an exemplary mask inspection system including an obscured optic configuration having two mirrors.

FIG. 5A illustrates an exemplary inspection system 500 including an obscured optic configuration. In this embodiment, inspection system 500 includes two mirrors M1 and M2, which reflect light beams from a mask 501 to substantially a point on a detector 502. Note that in this configuration, the light beam 503 passes through both mirrors M1 and M2 (via holes in their centers, which are not shown for convenience). Thus, the illumination source can be characterized as originating from substantially the same position as detector 502. Because detector 502 cannot collect light at the center, which is where the illumination is introduced to inspection system 500, the configuration is characterized as obscured. The prescription for the optic design shown in FIG. 5A is shown in a table 510 of FIG. 5B. The conic data (CC) and polynomial aspheric data (AD, AE, AF, AG) of specific surfaces, i.e. 3 and 5, are shown in a table 520 of FIG. 5C.

In this configuration, inspection system 500 can provide a 750× magnification and has a 0.25 NA.
Inspection system 500 can provide a wavefront correction of better than 0.03 waves rms (at 13 nm) over a 74 mm×18.5 mm detector plane. In this embodiment, the distance from mask 501 (OBJ) to detector 502 is approximately 2-3 m.

The prescription for another embodiment of the obscured optic design shown in FIG. 5A is shown in a table 610 of FIG. 6A. This optic configuration is infinity corrected and has a 100μ field size. The conic and polynomial aspheric data of specific surfaces, i.e. 4 and 6, are shown in a table 620 of FIG. 6B.

The prescription for a four-mirror, obscured optic configuration is shown in a table 710 of FIG. 7A. The conic and polynomial aspheric data of specific surfaces, i.e. 4 and 6, are shown in a table 720 of FIG. 7B. In this configuration, an EUV inspection system can provide a 100× magnification and has a 0.25 NA. Such an inspection system can provide a wavefront correction of better than 0.03 waves rms (at 13 nm) over a 74 mm×18.5 mm detector plane. The field of view at the inspection plane is 110 microns. The distance from object to image in this instance is 3015 mm. Note that because the optic design uses oblique (obscured) illumination, it can be used for dark field applications.

In one embodiment, back-thinned silicon time delay integration (TDI) sensor modules (described in further detail below) can be used for the detectors in the above-described inspection systems/aerial imaging systems. Current back-thinned TDI sensor modules are typically limited in size to roughly several thousand pixels in each x- and y-dimension. The use of these sensors at the required sensitivity (with physical pixels sizes of roughly 16 microns by 16 microns, needed to provide full wells sufficient to minimize shot noise in the resulting images) result in fields of view of the full TDI images at the mask plane on the order of 100-200 microns (with individual pixel dimensions of tens of nanometers at the inspection plane). The light reflected (or transmitted if a transmissive EUV mask) from the inspection plane is collected at high NA in order to provide high sensitivity, thereby ensuring that valuable EUV light can be used at high efficiency.

Because the EUV plasma is also collected with high NA for reasons of efficiency, the EUV plasma itself must have dimensions on the order of 100-200 microns in diameter. Therefore, the much smaller illumination area of the patterned mask inspection system requires a much different etendue than is required for EUV steppers.

To produce very bright and efficient EUV plasmas of these dimensions using practical subsystems, it is necessary that the laser producing the plasma deliver its energy in a time which is less than the time it takes an EUV laser produced plasma (temperatures of 20-50 keV) to expand from the initial target size to a dimension exceeding 100-200μ in diameter. While $CO_2$ lasers with pulse lengths on the order of 20-25 ns may be adequate for producing EUV light with etendues matching those of EUV lithography systems, they are not adequate for the EUV mask inspection application described here. Exemplary techniques for illuminating a specimen using plasma are described in U.S. Pat. No. 7,705,531, issued Apr. 27, 2010 to KLA-Tencor Technologies Corp., and incorporated by reference herein.

Because the plasma expansion velocity is roughly 50-100 microns per nanosecond in EUV plasmas, and because the critical density for absorption of $CO_2$ radiation is low enough that much of the $CO_2$ plasma is absorbed in the corona of the expanding EUV plasma, these mid-IR lasers are not suited to EUV inspection systems. Similarly, conventional Q-switched one micron wavelength lasers (with each pulse often being tens of nanoseconds and longer depending upon laser gain and cold cavity decay times), will only have the front end of the laser pulse absorbed in the plasma as the (temporal) tail of the pulse will view an expanding plasma with density below that required for efficient one micron wavelength absorption. The result will be a very low conversion efficiency of one micron to 13 mm light, for example, much below one percent.

To date, the most efficient laser produced plasmas are either Sn or Xe based (and to a degree Li based) plasma with conversion efficiencies in the range of 2-6%. Assuming a conversion efficiency of 1-2% from a EUV source of either Sn or Xe (or Li) pumped by a one kilowatt average power (e.g. 1-4 nsec pulse one micron wavelength laser), collected over a substantial solid angle (e.g. a solid angle of 5 radians) and delivered to the intermediate focus by this same optic, in-band EUV radiation at 13.4 mm (+/−2% bandwidth) on order of 3-10 watts can be provided.

For the target (e.g. the Sn or Xe) to effectively absorb the one micron wavelength pump radiation, the target should contain a suitable number of EUV emitting species. Therefore, the target size should be matched to the pump source to a) provide sufficient absorbers, b) minimize debris (not too many absorbers), and c) provide an EUV plasma diameter of 100-200 microns in diameter. The minimal source size is derived by recognizing that in order to sufficiently heat plasma, peak powers of roughly $5 \times 10^{10}$-$10^{11}$ W/cm2 are required. Thus, a one micron wavelength source will be delivered (using moderate NA optics) to a spot size approximating 10 microns (assuming the one micron wavelength source is near diffraction limited, and assuming a practical pulse width limit on the order of 1 ns).

Exemplary materials for photon generation providing the appropriate source size include Xe, Sn, Li, or these materials doped into a low Z carrier material (also called a mass-limited source as described by those skilled in the art). In one embodiment, generating these compact plasmas can be done by using short pulses (less than 3 or 4 nsec) from either a one micron wavelength (Yb or Nd based) or harmonically converted (to near 0.5 micron) Yb or Nd based laser operating at repetition rates in excess of 5 kHz, preferably in the range of 25-100 kHz and at average powers of between 1-3 kilowatts. The droplet sizes used in this source are typically less than 50 micron droplets and preferably in the range of 30 microns in diameter.

Advantageously, the laser driver technology described above can provide a very high brightness, laser-pumped EUV plasma. This plasma can efficiently provide radiation/illumination of the required etendue for EUV mask/wafer inspection. This laser produced plasma (LPP) light source can be coupled with practical, manufacturable reflective EUV optics, which can provide the high magnifications needed for high resolution inspection/aerial imaging of EUV masks/wafers.

Other light sources for a EUV inspection system can include a discharge produced plasma (DPP) light source (high power, low brightness) or a plasma lens light source (low power, intermediate brightness). Exemplary DPP light sources are being developed by XTREME technologies (a subsidiary of Ushio, Inc. of Tokyo, Japan). Exemplary commercially available plasma lens light sources are provided by Nano-UV of Courtaboeuf, France. Note that exemplary commercially available LPP light sources are provided by Cymer, Inc. of San Diego, Calif., or by Gigaphoton, Inc. of Oyamashi, Japan.

In one embodiment, the detector can be implemented with a plurality of TDI sensor modules. Each TDI sensor module can advantageously include localized circuitry for driving and signal processing. A module array including these TDI sensor modules can increase device manufacturability while decreasing driving and processing requirements relative to a large monolithic device of equivalent area. Exemplary TDI sensor modules and modular arrays are described in U.S. patent application Ser. No. 12/575,376, entitled "TDI Sensor Modules With Localized Driving And Signal Processing Circuitry For High Speed Inspection", which was filed by KLA-Tencor Corporation on Oct. 7, 2009 and is incorporated by reference herein.

Figure 8A:
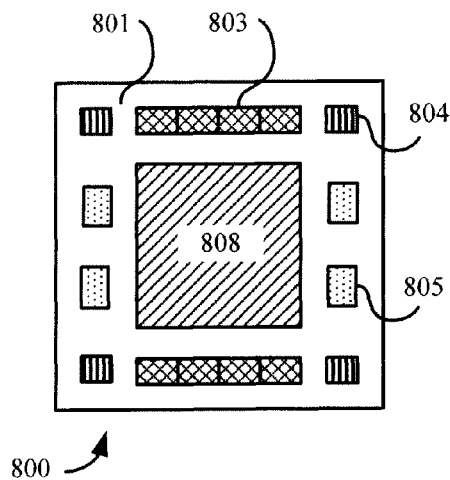
FIG. 8A illustrates a top view of an exemplary TDI sensor module that includes localized driving and signal processing circuitry.

FIG. 8A illustrates a top view of an exemplary TDI sensor module 800 that includes localized driving and signal processing circuitry (also called localized circuits herein). Specifically, TDI sensor module 800 includes a TDI sensor 802, processing circuits 803 for processing the signals from TDI sensor 802, timing and serial drive circuits 804, and pixel gate driver circuits 805.

In one embodiment, processing circuits 803 can provide correlated double sampling (CDS) and other analog front end (AFE) functions (e.g. analog gain control), analog to digital conversion (ADC), and digital post-processing such as black-level correction, per pixel gain and offset corrections, linearity corrections, look-up tables (LUTs), and data compression. The processing may be fixed or rely on additional, possibly real-time, input from the inspection system to perform functions such as sub-pixel interpolation, analog gain control to prevent digital saturation, image position shifting, and image spatial distortion correction. In one embodiment, local processing circuits 803 can manipulate various captured images in the analog or digital domain (described in further detail below), thereby saving communication and processing bandwidth in an image analysis computer of the inspection system.

The timing and serial drive circuits 804 can control clock timing and drive for TDI. Features such as reset pulse generation, multi-phase serial-register clock generation, and ADC synchronization may be included. This allows for very accurate timing which is needed to achieve high SNR (signal to noise ratio) at high clocking speeds.

The pixel gate driver circuits 805 provide slower but higher-current TDI gate drive signals to synchronize data capture with the inspection image motion and with other TDI sensors. Pixel gate driver circuits 805 may typically provide three-phase or four-phase drive waveforms of square-wave and/or sinusoidal waveforms. More generally, pixel gate driver circuits 805 may use digital-to-analog conversion to provide arbitrary function generation in order to optimize the charge transfer, thermal dissipation, and SNR of the sensor. U.S. patent application Ser. No. 10/992,063, entitled "Continuous Clocking Of TDI Sensors", which is incorporated by reference herein, describes this digital-to-analog conversion in greater detail.

Advantageously, localized driving circuits mean that each TDI sensor module has its own individual set of drivers (i.e. drivers 804 and 805). These individual drivers require significantly less current, and thus can be significantly smaller than conventional large-area TDI sensor drivers. Notably, locally distributing high fidelity, high-current waveforms from a plurality of small drivers (associated with the TDI sensor modules) is much more scalable than distributing waveforms from one large driver, even when the total current requirement is the same.

Figure 8B:
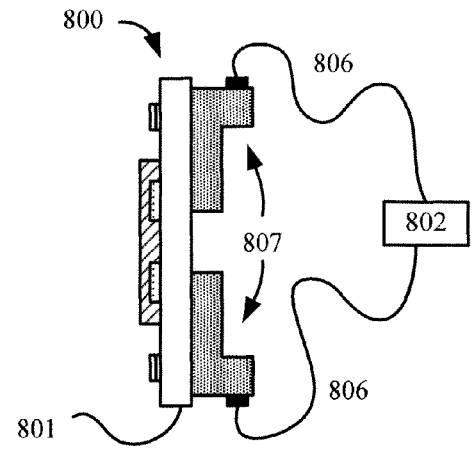
FIG. 8B illustrates a side view of an exemplary PCB including data transceivers connected to the PCB, wherein the PCB includes wiring in communication with the driving/processing circuits of the TDI sensor module.

In one embodiment, each of processing circuits 803, timing and serial drive circuits 804, and pixel gate drive circuits 805 can be implemented on integrated circuits positioned around TDI sensor 802 on a PCB (printed circuit board) 801. Note that the number of ICs used to implement the driving/processing circuits can vary based on embodiment. In one embodiment, PCB 801 can be implemented using a multi-layer, ceramic substrate. FIG. 8B illustrates a side view of an exemplary PCB 801 including data transceivers 807 (e.g. 10 Gigabit optical transceivers) connected to PCB 801, wherein PCB 801 includes wiring (not shown for simplicity) in communication with the driving/processing circuits of TDI sensor module 800. Note that the PCB may also provide an ultra-high-vacuum interface for the sensor system and allow signals and power to pass between a high-quality vacuum region on the sensor side and a low-quality vacuum region or a region near atmospheric pressure on the fiber side. In one embodiment, optical fibers 806 can be attached to data transceivers 807 to allow communication of driving/processing data between TDI sensor module 800 and system-level inspection components 808. In another embodiment, digital data from TDI sensor module 800 can be transmitted offboard using low voltage differential signaling (LVDS), or similar electrical signaling and digital multiplexing. The specific protocol can be selected from an industry standard or prescribed by those skilled in the art of electronic or optical high-speed digital communications.

Figure 9:
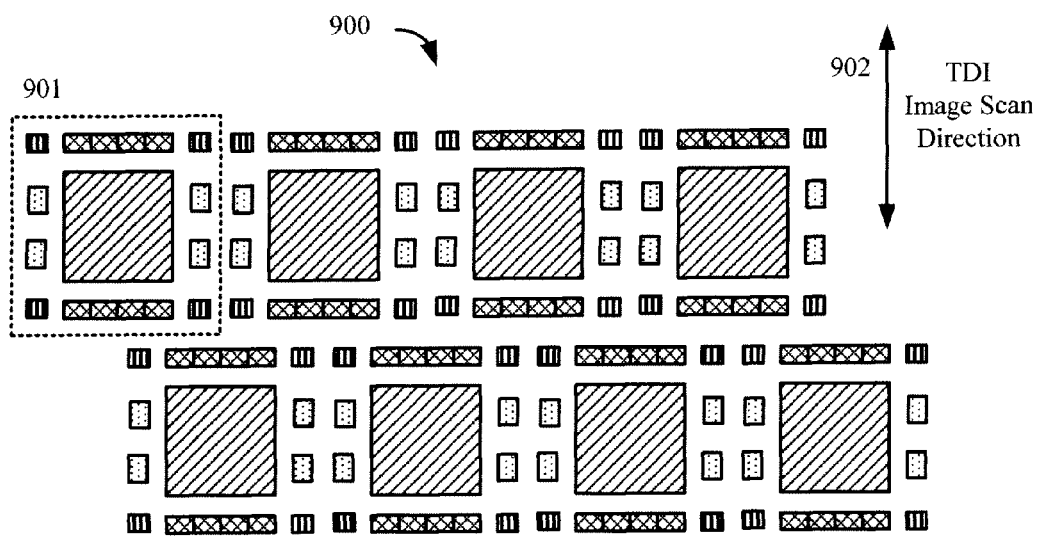
FIG. 9 illustrates an exemplary modular array of the TDI sensor modules for high speed configurations.

FIG. 9 illustrates an exemplary modular array 900 of TDI sensor modules 901 (also called a sensor module array). Note that the driving/processing circuits positioned around the TDI sensor take up a predetermined space. Thus, the TDI sensors in adjacent rows can be aligned such that at least 100% image coverage is achieved when used in a continuous scanning configuration. For example, in the embodiment shown in FIG. 9, the upper row can be offset with respect to the lower row such that the TDI sensor is positioned in the gap produced by the driving/processing circuits of an adjacent row. To ensure no gaps in image coverage, the width of each TDI sensor is equal to or greater than the space between TDI sensors. In this configuration, as the inspected wafer/mask/reticle is being moved in a TDI image scan direction 902, sensor module array 900 can ensure 100% EUV wavelength image capture.

In one embodiment, some minimal overlap between TDI sensors from adjacent rows can provide redundant data. This redundant data can, for example, ensure accurate alignment of the image data generated by TDI sensor modules 901. In one embodiment of minimal overlap, the inspection system can arbitrarily select the data from one TDI sensor module to be used for the edge pixels. In another embodiment, a detection system can combine and align, using sub-pixel digital processing, the data from multiple TDI sensor modules, to achieve improved quality data near edge pixels.

Note that the effective data rate for modular array 900 can be significantly higher than a single, large TDI sensor. This rate is achieved because the modular array can have an effective total size and number of output channels that are larger than can be practically manufactured in a single TDI sensor. Further note that any number of rows of TDI sensor modules can be included in a modular array, i.e. TDI sensor modules facilitate scaling. This scaling yields additional system flexibility and performance.

Figure 10:
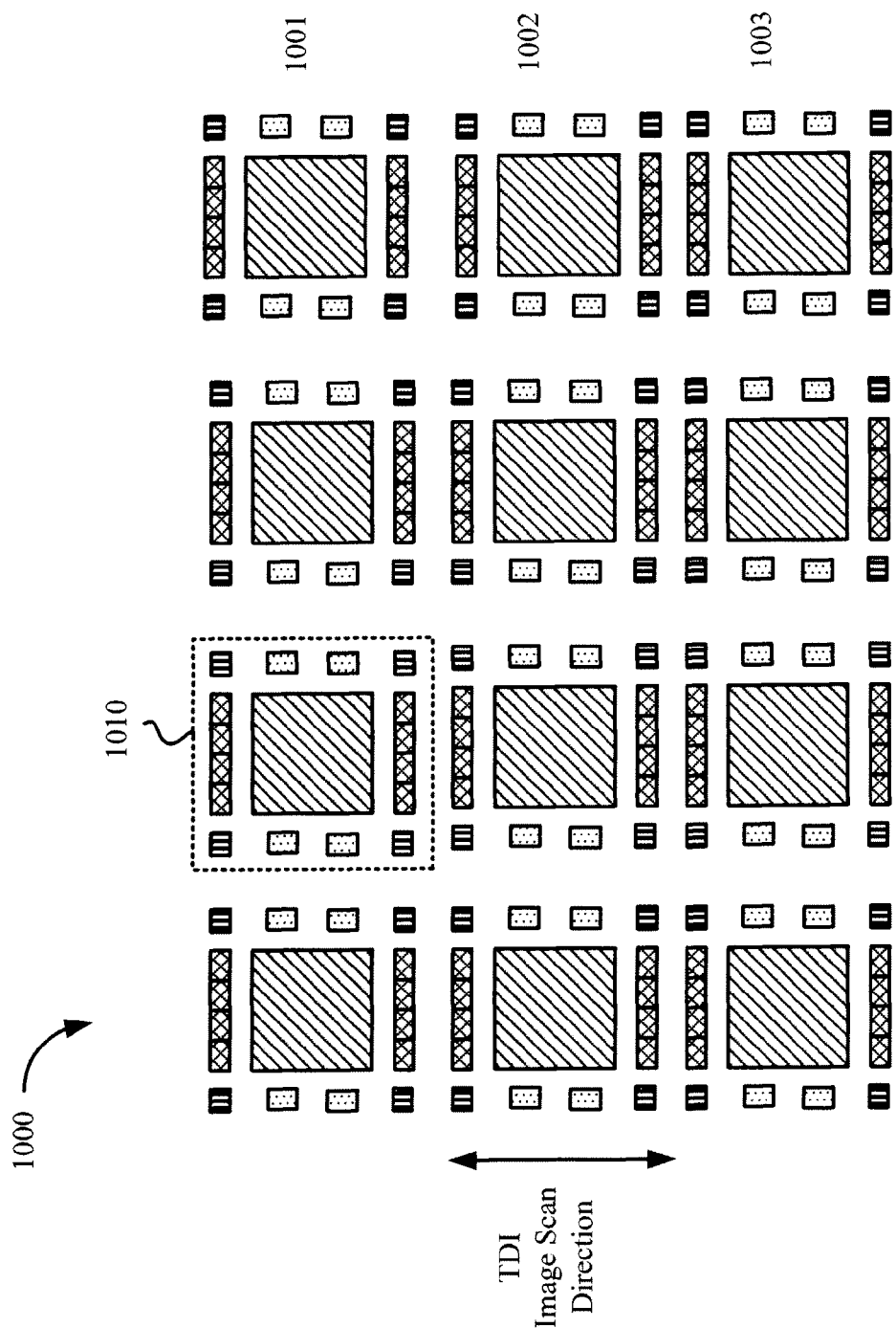
FIG. 10 illustrates an exemplary modular array of the TDI sensor modules for high integration configurations.

In another embodiment, integration of the detected data can be increased by aligning columns of the TDI sensor modules. For example, FIG. 10 illustrates an exemplary modular array 1000 including three rows 1001, 1002, 1003, and 1004 of TDI sensor modules 1010. In this embodiment, rows 1001-1003 capture and process samples of the same (or very similar) optical image data. Thus, modular array 1000 can advantageously provide a data stream for each swath of the inspected wafer/mask/reticle. This integration can minimize the fluctuations associated with a plasma light source (inherently unstable because of its shot generation), which would otherwise cause inspection difficulties. This configuration can also reduce the uniformity and stability requirements of the plasma light source subsystem which improves the manufacturability and operating lifetime of the inspection system.

Other portions of the inspected surface missed by the gap between sensors in this embodiment can be inspected by a shift (left or right) of the wafer/mask/reticle by the gap distance, and then performing another TDI image scan to cover another swath. This is called an interleave configuration. Note that the spacing between columns of the TDI sensor modules can be varied by compensating for the number of TDI image scans, i.e. the greater the spacing, the greater the number of TDI image scans (and thus, the number of swaths). Further note that even a single row of TDI sensor modules can be used in some embodiments, wherein the spacing between TDI sensor modules determines the number of swaths necessary to provide 100% inspection coverage.

Figure 12:
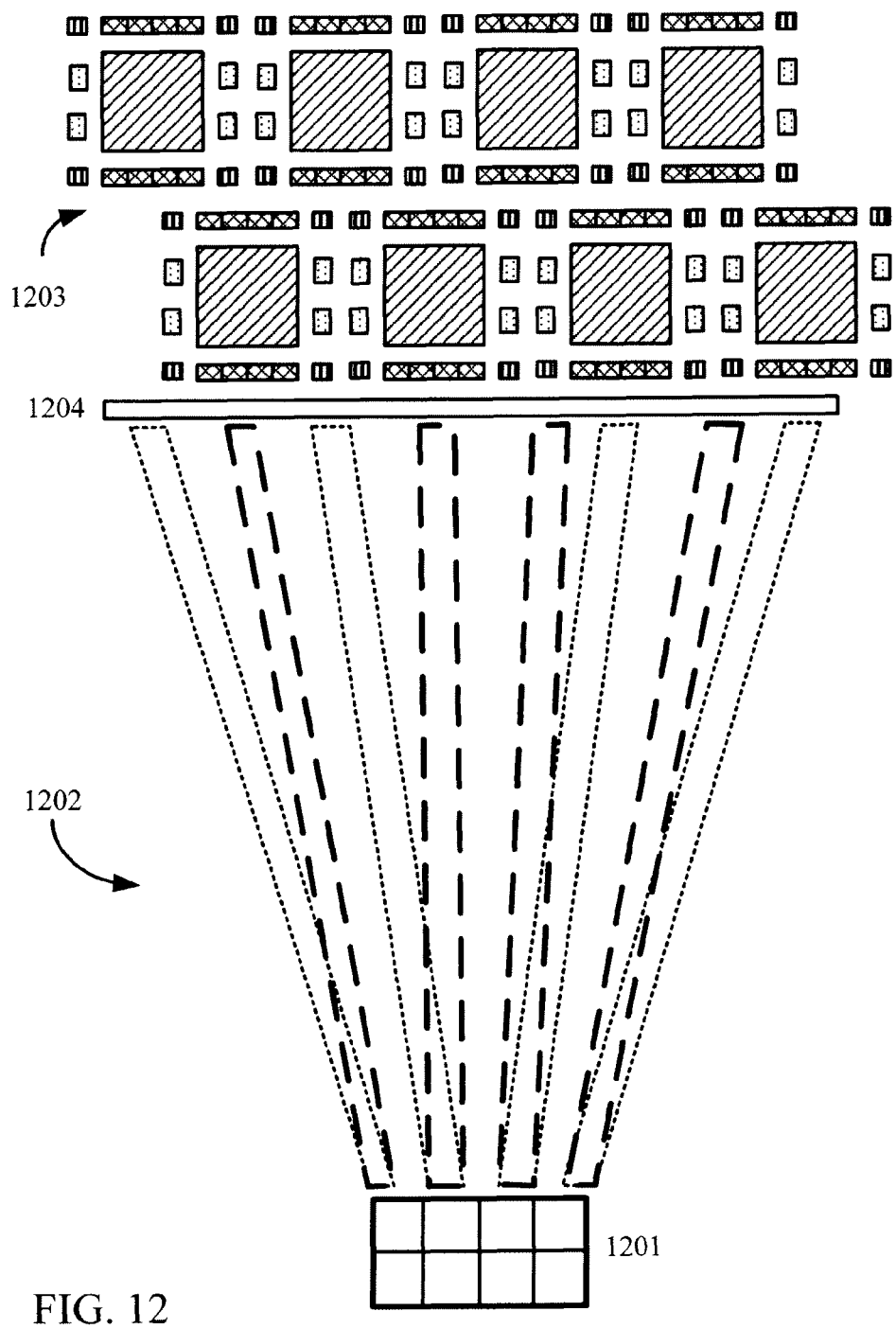
FIG. 12 illustrates another exemplary hollow light pipe configuration in relation to the TDI sensors of the modular array.

One advantage of using modular arrays for EUV inspection is that the inspected surface, i.e. the wafer, mask, or reticle, need only be partially illuminated (described in further detail in reference to FIG. 12). This dispersed illumination can advantageously also disperse the heat associated with the illumination, thereby allowing heat to more quickly dissipate to adjacent cooler areas and thus reduce the potential of damaging the inspected surface during high-speed inspection.

Another advantage of using modular arrays is an increased signal-to-noise ratio (SNR). Note that for visible light, the energy of the photon is generally sufficient to excite one electron into a conduction state. That is, one photon typically results in not more than one signal-generating electron. However, as the energy of the photon becomes higher, additional electrons can enter into a conduction state and be collected. For example, at EUV (13 nm), the energy of one photon is sufficient to excite approximately 25 electrons into a conduction state. So, for a given TDI sensor electron well capacity per pixel, the maximum photon detection level is effectively 25 times less for EUV light. Also, because the image SNR for photon shot noise is proportional to the square root of the collected photons, the SNR will be lower for the EUV case compared to the visible light case.

The above-described modular array can advantageously improve the noise characteristics of the inspection system (i.e. the SNR). Specifically, having two TDI sensor modules collecting redundant image data can improve the SNR by a square root of 2 and, by extension, having N TDI sensor modules collecting redundant data can improve the SNR by a square root of N.

An additional advantage of using modular arrays can be found with low-brightness illumination. FIGS. 11A and 11B illustrate exemplary hollow optical homogenizer, or "light pipe" configurations that can be used with the modular arrays discussed above. In these configurations, a low-brightness source illumination can be efficiently distributed to a plurality of TDI sensor modules. For example, the light pipe configuration of FIG. 11A includes a light source 1100, a collector 1101 that collects the light from light source 1100 and redirects the light to a main hollow light pipe 1102 using a "reflecting lens" known in the art. Note that the collector required for EUV wavelengths may be composed of reflecting shells, similar to the Fresnel lens principal. A plurality of turning light pipes 1103 (two shown) direct equal portions of the light from main light pipe 1102 into associated distribution light pipes 1104. The light from distribution light pipes 1104 can be used to illuminate two TDI sensor modules of a modular array (not shown for simplicity).

Light pipes 1102 and 1103 can be formed using appropriate materials for EUV. For example, hollow reflective-type light pipes can be used for EUV illumination. Note that grazing-incidence reflection optics can be used for EUV illumination to control both light distribution and uniformity. Unnecessary reflections reduce the total light efficiency of the system, so there is a trade-off between improved illumination uniformity and illumination power requirements. The minimum light-pipe length that produces required uniformity is desirable. A light-pipe homogenizer can be advantageous if the mirror reflection efficiencies are high, but is not strictly required for the inspection architecture.

FIG. 11B illustrates a light tube configuration including a mirror-based collector. Specifically, in this embodiment, a light source 1110 can direct its light to a mirror-based collector 1111, which in turn reflects and focuses that light to a main hollow light pipe 1112. A plurality of turning light pipes 1113 (two shown) direct equal portions of the light from main light pipe 1112 into associated distribution light pipes 1114. The light from distribution light pipes 1114 can be used to illuminate two TDI sensor modules of a modular array (not shown for simplicity).

Note that different light pipe configurations can be used for the specific modular array embodiment, i.e. the number of TDI sensor modules that are to be illuminated. For example, FIG. 12 illustrates a light pipe configuration including an aperture set 1201 (shown as an end view for clarity) to receive light and a plurality of light pipes 1202 (eight light pipes shown) for directing the light to a TDI modular array 1203. In this embodiment, light pipes 1202 are stacked in pairs, wherein each light pipe is aligned with a specific column of TDI sensors of modular array 1203 (in this configuration, eight columns) Specifically, the light pipes 1202 represented using dotted lines are aligned with columns associated with the top row of the TDI sensors in TDI modular array 1203, whereas the light pipes represented using dashed lines are aligned with columns associated with the bottom row of the TDI sensors in TDI modular array 1303. Notably, in aperture set 1201, each aperture, with a predetermined magnification, substantially matches a TDI sensor shape. In one embodiment, a shaping aperture array 1204 can include apertures for further masking the light emitted by each light tube. Note that shaping aperture 1204 can be used in all the embodiments including light pipes to ensure the emitted light has the same shape as the TDI sensors.

Figure 13:
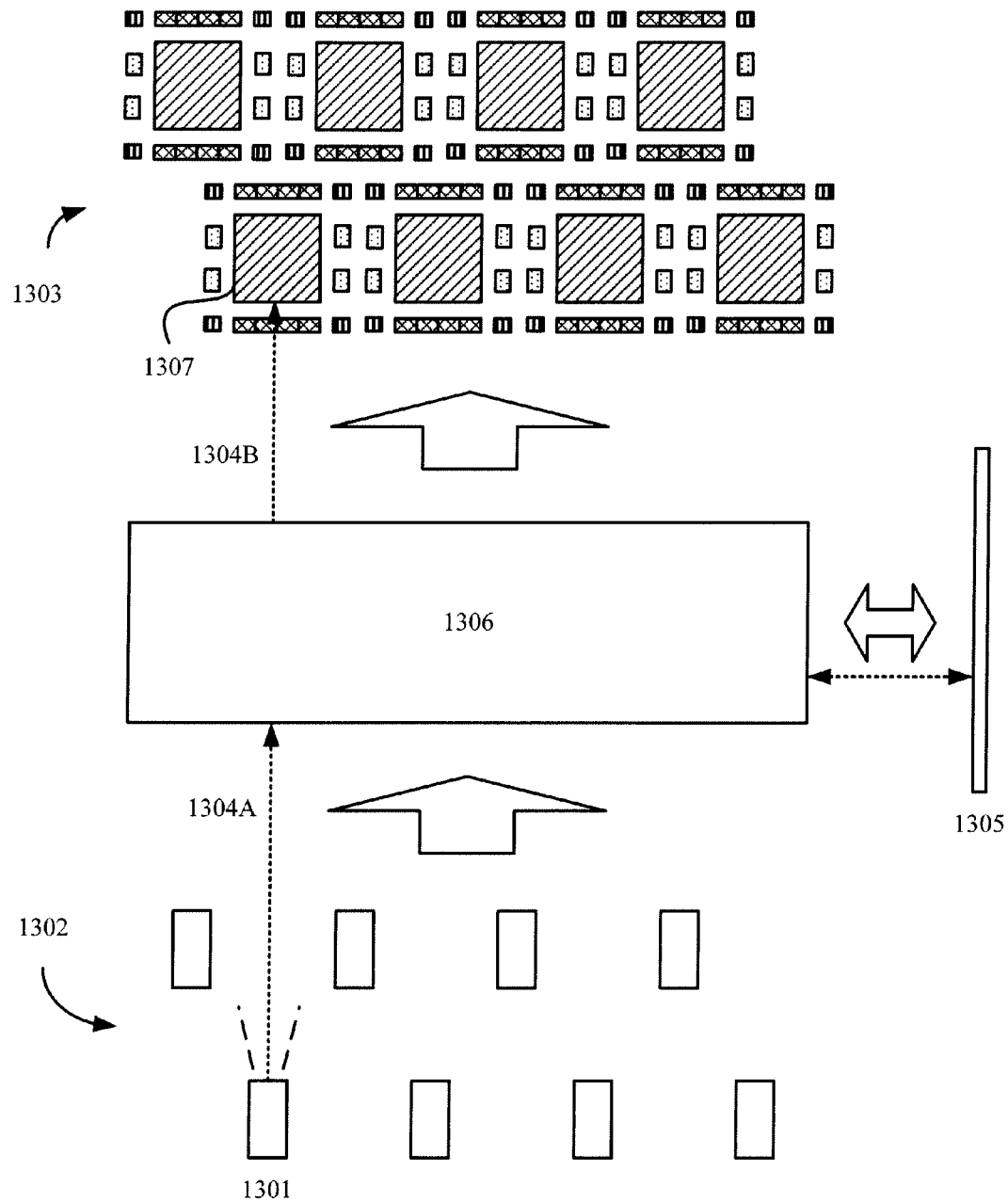
FIG. 13 illustrates an exemplary multiple-light-source configuration where there is a correspondence between each light source and sensor.

FIG. 13 illustrates a multiple light source configuration 1302 arranged so that each light source has a corresponding sensor. For example, an optic configuration 1306 can direct light 1304A from a light source 1301 to an inspected surface 1305. Optic configuration 1306 can further include one of the mirror configurations described above, which in turn directs the reflected light 1304B (which corresponds with light 1304A) from inspected surface 1305 to a sensor 1307. Thus, in this embodiment, optic configuration 1306 can direct the reflected light associated with one light source from inspected surface 1305 to a corresponding sensor in modular array 1303. This multiple light source can facilitate the use of lower brightness light sources while achieving the appropriate NA and magnification for EUV inspection.

Furthermore, for the case where multiple rows of sensors are used inspect the same region, the source center wavelengths for a group at one row can be tuned to a different wavelength relative to a group from a second row. This feature can provide enhanced material contrast and can be used advantageously to detect fabrication errors in EUV masks.

Figure 14:
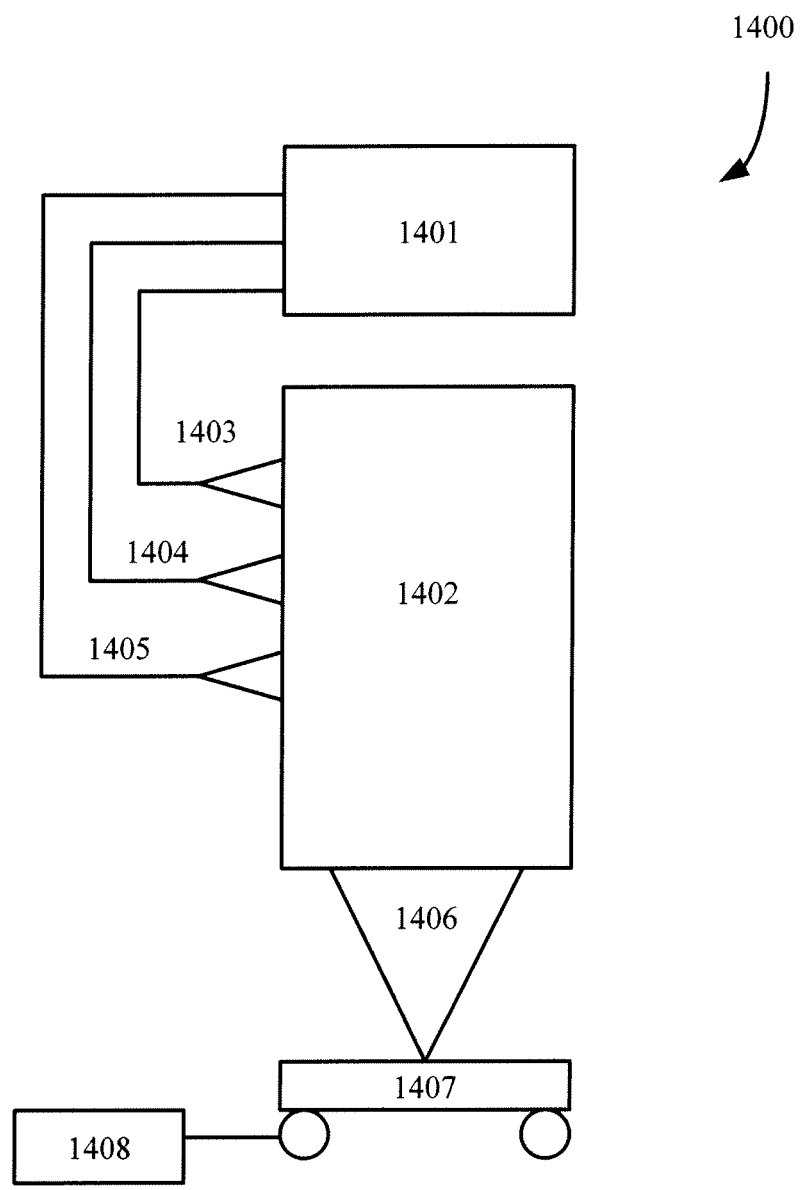
FIG. 14 depicts a simplified inspection system that can be used with the above-described modular array.

FIG. 14 depicts a simplified inspection system 1300 that can be used with the above-described modular array. An inspection surface 1407 is illuminated by any of the light pipe embodiments discussed above in reference to FIGS. 11-12. Inspection system 1400 also typically includes scanning apparatus 1408 that permits any desired portion of surface 1407 to be illuminated and inspected. Such scanning and illumination apparatus and methodologies are known to persons having ordinary skill in the art. Light 1406 from surface 1407 (reflected, scattered, diffracted, etc.) is received by an optical system 1402. Optical system 1402 is configured to receive light from surface 1407 and direct portions of the light onto a plurality of TDI sensor modules 1403, 1404, and 1405 arranged in one of the above-discussed configurations. Typically, optical system 1402 includes a plurality of optical elements (e.g., the above-described mirrors, objective lens systems, beam splitters, and other optical elements) arranged so that each of TDI sensor modules 1403, 1404, and 1405 can form a composite image of surface 1407. These images are transmitted as electronic or optical data signals to an image processor 1401 capable of a wide range of signal and image processing operations. In particular, image processor 1401 can be capable of image storage, image processing and reconstruction, as well as locating, quantifying, and categorizing defects located in the surface 1407.

Note that although TDI sensor modules and TDI sensor arrays are described above in detail, the EUV inspection system can include sensor modules/arrays performing flash-on-the-fly mode (which generates a series of static images) or conventional CCD (charge coupled device) frame transfer readout instead of TDI.

Although illustrative embodiments of the invention have been described in detail herein with reference to the accompanying figures, the embodiments described herein are not intended to be exhaustive or to limit the invention to the precise forms disclosed. As such, many modifications and variations will be apparent.

For example, the above-described inspection system can be easily expanded to achieve a higher NA. Specifically, one or more additional mirrors can be added to the optic configuration. These additional mirrors, which would have reflectivity greater than 60%, can increase the magnification, thereby increasing the resolution (and thus NA). Note that adding mirrors also lengthens the optical path.

Note that the above-described systems can be used to perform full NA dark field inspection. Alternatively, the bright field reticle inspection can be done by using part of the NA (e.g. half) for illumination. In dark field inspection, the specularly reflected light from the inspected surface is not collected. This imaging mode tends to increase contrast and sensitivity to scattering defects. In bright field inspection, the specularly reflected light is collected, which tends to enhance detection of subtle differences in reflectivity of objects. In another embodiment, a photocathode followed by an electromagnetic zoom can be used to boost magnification. The zoom subsystem may be constructed using an image intensifier or image converter tube design known in the art, with a suitable EUV-sensitive photocathode. Micro-channel plate based designs can also increase signal levels in light-starved applications.

The highest magnifications of the exemplary designs are suitable for review of extremely small defects and for observing nano-scale features of the inspected objects. Thus, high magnification capability is an advantage of these systems. Review requirements generally include higher magnification of inspected masks because the defects need to be better resolved compared to high-speed inspection, where the priority is often to quickly find the defects and their associated locations.

Note that although the specific optic configuration embodiments described above can advantageously provide an optic path approximately 2-3 meters long, other embodiments may have slightly longer or shorter paths. Therefore, a generic description of such optic configuration embodiments can be described as providing optics paths less than 5 meters.

Accordingly, it is intended that the scope of the invention be defined by the following Claims and their equivalents.

The invention claimed is:

1. An extreme ultraviolet (EUV) inspection system comprising:
    a light source directed to an inspected surface;
    a detector for detecting light deflected from the inspected surface, the detector including a plurality of sensor modules; and
    an optic configuration for directing the light from the inspected surface to the detector, the optic configuration including only mirrors, of which a plurality are aspheric, at least one of the mirrors having an aperture radius of at least 49 mm, the mirrors providing magnification of at least 100× within an optical path less than 5 meters long.

2. The EUV inspection system of claim 1, wherein the optical path is approximately 2-3 meters.

3. The EUV inspection system of claim 1, wherein the mirrors include:
    six mirrors in an unobscured configuration, the unobscured configuration directing light from the inspected surface to the detector in six bounces.

4. The EUV inspection system of claim 3, wherein the unobscured configuration provides a numerical aperture (NA) of 0.25 and a magnification of 1000×.

5. The EUV inspection system of claim 3, further including a double aperture component to shape a beam of light, thereby facilitating aerial inspection.

6. The EUV inspection system of claim 5, wherein the double aperture component includes an illumination aperture and a detection aperture, wherein an obscuration is provided in the detection aperture when EUV lithographic optics used in making the inspected surface employed a central obscuration.

7. The EUV inspection system of claim 3, wherein the detector includes a modular array, the modular array including the plurality of sensor modules in a single row.

8. The EUV inspection system of claim 3, wherein the detector includes a modular array, the modular array including the plurality of sensor modules positioned in at least two rows, wherein the sensor modules of one row are offset vertically with respect to the sensor modules of any adjacent row(s).

9. The EUV inspection system of claim 8, wherein the sensor modules of every other row are aligned vertically.

10. The EUV inspection system of claim 3, wherein the detector includes a modular array, the modular array including the plurality of sensor modules positioned in at least two rows, wherein the sensor modules of one row are vertically aligned with respect to the sensor modules of any adjacent row(s).

11. The EUV inspection system of claim 1,
    wherein the light source is a plasma having a diameter between 100-200 microns.

12. The EUV inspection system of claim 11, wherein the plasma is generated using a laser with an EUV emitter.

13. The EUV inspection system of claim 12, wherein the EUV emitter is one of tin, xenon, lithium, or a doped target using one of tin, xenon, or lithium.

14. The EUV inspection system of claim 13, wherein the laser is a one of a ytterbium-based and a neodymium-based laser operated at a repetition rate greater than 5 kHz and an average power between 1-4 kilowatts.

15. The EUV inspection system of claim 13, wherein the laser is operated using pulses less than 4 nsec to generate the plasma.

16. The EUV inspection system of claim 12, wherein the laser is one of a harmonically converted Yb-based laser and a Nd-based laser.

17. The EUV inspection system of claim 16, wherein the laser operates using first harmonics at nominally 0.5 microns.

18. The EUV inspection system of claim 17, wherein the laser uses pulses at nominally 2 nsec, and a repetition rate less than 100 kHz.

19. The EUV inspection system of claim 18, wherein the laser uses droplet sizes between 35-50 microns.

20. The EUV inspection system of claim 12, wherein illumination of the EUV emitter has a spot size between 30-50 microns.

21. The EUV inspection system of claim 1, wherein the light source includes a laser-produced plasma (LPP) light source.

22. The EUV inspection system of claim 1, wherein the light source includes a discharge produced plasma (DPP) light source.

23. The EUV inspection system of claim 1, wherein the light source includes a plasma lens light source.

24. The EUV inspection system of claim 1, wherein the light source includes a plurality of illumination sources.

25. The EUV inspection system of claim 24, wherein illumination center wavelengths of a group of the illumination sources differ by more than 3 nm from another group of the illumination sources.

26. The EUV inspection system of claim 1, wherein the light source distributes light on the inspected surface to facilitate lateral heat dissipation on the inspected surface.

27. The EUV inspection system of claim 26, wherein the light source includes a plurality of light tubes.

28. The EUV inspection system of claim 26, wherein the light source includes an aperture set, each aperture, with a predetermined magnification, substantially matching a sensor shape.

29. The EUV inspection system of claim 1, wherein the plurality of sensor modules perform at least one of time delay integration (TDI), flash-on-the-fly mode, and CCD (charge coupled device) frame transfer readout.

30. The EUV inspection system of claim 1, wherein the inspected surface is one of an EUV blank mask, an EUV patterned mask, and a patterned wafer fabricated using the EUV patterned mask.

31. The EUV inspection system of claim 1, wherein the mirrors include:
four mirrors in an unobscured configuration, the unobscured configuration directing light from the inspected surface to the detector in four bounces.

32. The EUV inspection system of claim 31, wherein the optic configuration provides a numerical aperture (NA) of 0.25 and a magnification of 100×.

33. The EUV inspection system of claim 31, further including a double aperture component to shape a beam of light, thereby facilitating aerial inspection.

34. The EUV inspection system of claim 33, wherein the double aperture component includes an illumination aperture and a detection aperture, wherein an obscuration is provided in the detection aperture when EUV lithographic optics used in making the inspected surface employed a central obscuration.

35. The EUV inspection system of claim 31, wherein the detector includes a modular array, the modular array including the plurality of sensor modules in a single row.

36. The EUV inspection system of claim 31, wherein the detector includes a modular array, the modular array including the plurality of sensor modules positioned in at least two rows, wherein the sensor modules of one row are offset vertically with respect to the sensor modules of any adjacent row(s).

37. The EUV inspection system of claim 36, wherein the sensor modules of every other row are aligned vertically.

38. The EUV inspection system of claim 37, wherein the light source includes a plurality of illumination sources.

39. The EUV inspection system of claim 37, wherein the light source includes plasma lens sources.

40. The EUV inspection system of claim 31, wherein the detector includes a modular array, the modular array including the plurality of sensor modules positioned in at least two rows, wherein the sensor modules of one row are vertically aligned with respect to the sensor modules of any adjacent row(s).

41. An extreme ultraviolet (EUV) inspection system comprising:
a light source directed to an inspected surface;
a detector for detecting light deflected from the inspected surface, the detector including a plurality of sensor modules; and
an optic configuration for directing the light from the inspected surface to the detector, the optic configuration providing magnification of at least 100× within an optical path less than 5 meters long, wherein the optic configuration includes:
one of a scintillator for converting EUV light into visible light and a photocathode for converting EUV light into electrons;
four mirrors in an unobscured configuration, the unobscured configuration directing light from the inspected surface to the scintillator/photocathode in four bounces; and
a magnifying system coupled between the scintillator/photocathode and the detector for further magnification.

42. The EUV inspection system of claim 41, wherein the optic configuration provides a numerical aperture (NA) of 0.25 and a magnification of 500×-10000×.

43. The EUV inspection system of claim 41, further including a double aperture component to shape a beam of light, thereby facilitating aerial inspection.

44. The EUV inspection system of claim 43, wherein the double aperture component includes an illumination aperture and a detection aperture, wherein an obscuration is provided in the detection aperture when EUV lithographic optics used in making the inspected surface employed a central obscuration.

45. The EUV inspection system of claim 41, wherein the detector includes a modular array, the modular array including the plurality of sensor modules in a single row.

46. The EUV inspection system of claim 41, wherein the detector includes a modular array, the modular array including the plurality of sensor modules positioned in at least two rows, wherein the sensor modules of one row are offset vertically with respect to the sensor modules of any adjacent row(s).

47. The EUV inspection system of claim 46, wherein the sensor modules of every other row are aligned vertically.

48. The EUV inspection system of claim 41, wherein the detector includes a modular array, the modular array including the plurality of sensor modules positioned in at least two rows, wherein the sensor modules of one row are vertically aligned with respect to the sensor modules of any adjacent row(s).

49. An extreme ultraviolet (EUV) inspection system comprising:
a light source directed to an inspected surface;

a detector for detecting light deflected from the inspected surface, the detector including a plurality of sensor modules; and an optic configuration for directing the light from the inspected surface to the detector, the optic configuration providing magnification of at least 100× within an optical path less than 5 meters long, wherein the optic configuration includes two mirrors in an obscured configuration, the obscured configuration directing light from the inspected surface to the detector in four bounces.

50. The EUV inspection system of claim 49, wherein the optic configuration provides a numerical aperture (NA) of 0.25 and a magnification of 750×.

51. The EUV inspection system of claim 49, further including a double aperture component to shape a beam of light, thereby facilitating aerial inspection.

52. The EUV inspection system of claim 51, wherein the double aperture component includes an illumination aperture and a detection aperture, wherein an obscuration is provided in the detection aperture when EUV lithographic optics used in making the inspected surface employed a central obscuration.

53. The EUV inspection system of claim 49, wherein the detector includes a modular array, the modular array including the plurality of sensor modules in a single row.

54. The EUV inspection system of claim 49, wherein the detector includes a modular array, the modular array including the plurality of sensor modules positioned in at least two rows, wherein the sensor modules of one row are offset vertically with respect to the sensor modules of any adjacent row(s).

55. The EUV inspection system of claim 54, wherein the sensor modules of every other row are aligned vertically.

56. The EUV inspection system of claim 49, wherein the detector includes a modular array, the modular array including the plurality of sensor modules positioned in at least two rows, wherein the sensor modules of one row are vertically aligned with respect to the sensor modules of any adjacent row(s).

* * * * *